United States Patent
Shchervinsky

[19]
[11] Patent Number: 6,021,355
[45] Date of Patent: Feb. 1, 2000

[54] SURGICAL ELECTRODE HAVING A PARTIALLY INSULATED NEEDLE

[75] Inventor: Semyon Shchervinsky, Whitehouse Station, N.J.

[73] Assignee: Ethicon, Inc., Somerville, N.J.

[21] Appl. No.: 09/182,723

[22] Filed: Oct. 29, 1998

[51] Int. Cl.[7] ................................................. A61N 1/05
[52] U.S. Cl. .......................................................... 607/132
[58] Field of Search .................................. 607/132, 115, 607/119, 126

[56] References Cited

U.S. PATENT DOCUMENTS

| | | | |
|---|---|---|---|
| 3,760,332 | 9/1973 | Berkovits et al. | 339/66 R |
| 4,010,756 | 3/1977 | DuMont et al. | 128/404 |
| 4,072,154 | 2/1978 | Anderson et al. | 128/419 |
| 4,442,840 | 4/1984 | Wojciechowicz, Jr. | 128/419 P |
| 4,630,617 | 12/1986 | Ritter et al. | 128/784 |
| 5,795,178 | 8/1998 | Schilder et al. | 439/417 |

*Primary Examiner*—Scott M. Getzow

[57] ABSTRACT

A surgical electrode of the type used as a temporary cardiac pacing wire provides electrical contact between a patient's heart and a source of electrical pulses (i.e., a pacemaker). One end of the wire attaches to the heart. The other end is attached to a surgical needle that has a weakened zone in its shaft, to permit the sharp end of the needle to be broken off and discarded. The remaining shaft connects to the pacemaker. By providing an insulating coating over part of the shaft, the electrode of the invention protects against harm to the patient that would otherwise be caused by misconnecting the electrode or by shorting the two electrodes that comprise a setup.

10 Claims, 1 Drawing Sheet

SURGICAL ELECTRODE HAVING A PARTIALLY INSULATED NEEDLE

BACKGROUND OF THE INVENTION

1. Field of the Invention

This invention relates to a surgical electrode and, more particularly, to a temporary cardiac pacing wire having a partially insulated needle to enhance its safety.

2. Description of the Related Art

Devices to stimulate or regulate cardiac function have been known and used for decades. They involve a power source (pacemaker) and a surgical electrode to attach the source to the heart. They are generally of two types.

Implantable pacers are intended for long-term use and, as the name suggests, are entirely implanted in the body. The other type is intended for temporary use. The pacemaker is located outside the body and is connected to the heart by a surgical electrode called a "temporary pacing wire". Although surgical electrodes are used for preparing electrocardiograms and other applications, for the sake of brevity, the description that follows is focused on temporary cardiac pacing wires. In general, such connectors are constructed of a number of fine, stainless steel wires twisted together to form a single, flexible, multifilament electrode wire. The major portion of the wire is insulated with a polyethylene, polytetrafluoroethylene, silicone, nylon, or other non-conducting coating, with a short length of wire at either end left uninsulated. To one uninsulated end of the electrode wire there is attached by swaging or other means a fine curved needle for piercing the heart tissue to place the uninsulated end of the electrode in the myocardium. At the other end of the electrode wire is affixed a straight (e.g., Keith-type) cutting needle for piercing the thoracic wall to lead the electrode to an outer point for connection with the pacemaker. Once that has been accomplished, the needle, or the sharp, pointed end of it, is clipped off and the electrode is ready to be attached to the pacemaker as required to stimulate or regulate the beating of the heart. A single setup involves two electrodes; i.e., two temporary pacing wires.

Temporary pacing wires have been described in a number of patents. U.S. Pat. No. 4,010,756, issued on Mar. 8, 1977 to DuMont et al., discloses a surgical electrode that has a weakened zone in the straight needle that pierces the body when the pacing wire is put in place. The weakened zone permits the pointed end of the needle to be snapped off and the remaining shank to be used as a jack and connected to a pacemaker. A disadvantage of this design is that the shank end can have a burr that could cause minor injuries to a healthcare worker. A more serious concern is that the bare shank could inadvertently be inserted into an inappropriate power source (such as a wall outlet) with very serious consequences. Another danger is that the two electrodes of a setup, protruding from a pacemaker, could be accidentally shorted; for example, by a surgical instrument.

U.S. Pat. No. 4,442,840, issued on Apr. 17, 1984 to Wojciechowicz, discloses a connector that attaches to the shank of the straight needle after it has been clipped or broken off from the sharp end. The connector can then be connected to a mating receptacle on a medical instrument for diagnosis or therapy. (Another type of connector for a temporary pacing wire is disclosed in U.S. Pat. No. 5,795,178, issued on Aug. 18, 1998 to Schilder et al.) Connectors that attach to the free end of a temporary pacing wire (after the sharp end of the straight needle has been removed) provide some advantages, but they require additional effort to attach and involve additional expense.

U.S. Pat. No. 4,630,617, issued on Dec. 23, 1986 to Ritter et al., discloses a surgical electrode whose straight-needle end has a blind hole or flange on the nonpointed end. The hole or flange holds a blunt-pointed pin with controlled pull-out characteristics. Thus, the pin can be pulled out and used as a jack for connecting to a pacemaker or other device. The fact that this device must contain a blunt-pointed pin within a member that necessarily has a larger diameter requires that the straight needle shaft be relatively large. This, in turn, increases the trauma caused when the needle passes through the thoracic wall during placement.

Prior art systems for connecting temporary pacing wires to pacemakers fall into two categories. Simple ("connector-free") systems pose actual and/or potential harm to the cardiac patient. Systems that use connectors require the additional step of attaching the connector, as well as the additional cost of the connector.

SUMMARY OF THE INVENTION

The present invention provides a temporary cardiac pacing wire that requires no connector for attaching it to a power source or diagnostic instrument. It nevertheless overcomes some of the drawbacks of connector-free systems of the prior art.

The partially insulated surgical electrode of the present invention comprises
  a) an electrically conductive wire,
  b) means for making electrical contact with a heart, attached to and in electrical contact with one end of the wire,
  c) a surgical needle in electrical contact with the opposite end of the wire, the surgical needle comprising
    i) a blunt first end and sharp second end, joined by a shaft, the first end being attached to the wire,
    ii) a predetermined point on the shaft, defining a first section lying between the point and the blunt end of the needle and a second section lying between the point and the sharp end of the needle, and
    iii) an electrical insulator that extends around the shaft from a first location in the first section at least to the predetermined point.

DETAILED DESCRIPTION OF THE INVENTION

This invention relates to a temporary cardiac pacing wire (tcpw) that attaches directly to a pacemaker, but is safer to use than earlier versions that also did not require connectors for attaching to a pacemaker. By not requiring a connector, the present tcpw saves time and expense for the healthcare provider.

Figure 1:
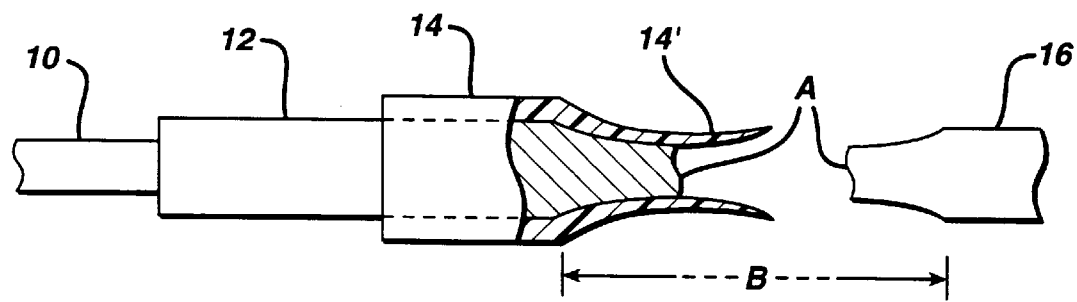
FIG. 1 is a plan view in partial cross section of a part of the temporary pacing wire of the present invention.

The present invention can be understood by referring to FIG. 1, which depicts a plan view in partial cross section of the relevant part of a tcpw. Electrode wire 10 is attached, by swaging or by other means well known in the art, to the unpointed end of needle 12. When the tcpw is in place, the other end of electrode wire 10 (not shown) is attached to a patient's heart. The procedure for placing the tcpw in the heart is described in U.S. Pat. No. 4,010,756, hereby incorporated herein by reference.

Insulator 14 covers needle 12 on both sides of the break that occurred at surface A, which took place within optional weakened zone B. Note that for clarity, weakened zone B is shown greatly enlarged. Details of weakened zones are provided in the above-referenced U.S. Pat. No. 4,010,756. The break served to separate the pointed section 16 of needle 12. If weakened zone B is absent, the needle and insulation are cut by conventional means at an insulated point on the shaft. In that case, the insulator does not extend beyond the cut end at A. A weakened zone is preferred, because, as FIG. 1 shows, the break in needle 12 does not cause a break in insulation 14. Preferably, insulator 14 is flexible, not brittle, and does not bind too closely to needle 12, so that it remains intact when needle 12 is broken and the pointed section 16 discarded (point not shown). Preferably, to ensure that insulator 14 remains intact, it extends only a short distance beyond weakened zone B into pointed section 16. More preferably that distance is about 0.1 mm to about 1 mm.

After the break, flap 14' of insulator 14 extends beyond the broken end of the shaft of needle 12. The insulating flap protects the cardiac patient if the free end of the temporary cardiac pacing wire is inadvertently inserted into a power source other than the intended pacemaker. It also protects persons that handle the temporary cardiac pacing wire from possible minor injury that might otherwise result from contact with a rough surface A.

A variety of organic and inorganic insulating materials are well known and suitable for insulator 14. The insulator may be applied to the wire by extrusion, injection molding, or any other suitable process. Coating is a preferred process. It is convenient to refer to "coatings" of these materials, whether or not they are bonded to the wire. Suitable insulators include coatings of poly-xylylene, fluoropolymers, nylon, vinyl, epoxy, urethane, polyamide, polyester, acrylic, silicone, phenylene sulfide, and polyamideimide. Poly-xylylene (Parylene®) is a preferred coating, because it is suitable, available, and inexpensive. The coating can be applied by any of a number of methods, well known in the coating art. Suitable methods include anodizing, oxidation, vacuum deposition, electrostatic spray (gas, liquid, or powder), and conventional liquid coating. An insulator can also be provided using shrink-fit tubing. Of course the preferred method of application depends on the material. Parylene is preferably coated by vacuum deposition. (Coating services are available from Vitek Research Corp., Derby, Conn.) Depending on the choice of material, pre-treatment of the surface may also be desirable or necessary, before insulator 14 is applied. These pretreatments, well known in the art, are selected from among ultrasonic, abrasive, cold gas plasma, and vapor degreasing. In practice, simple experimentation will yield optimum materials, methods, and parameters.

Figure 2:
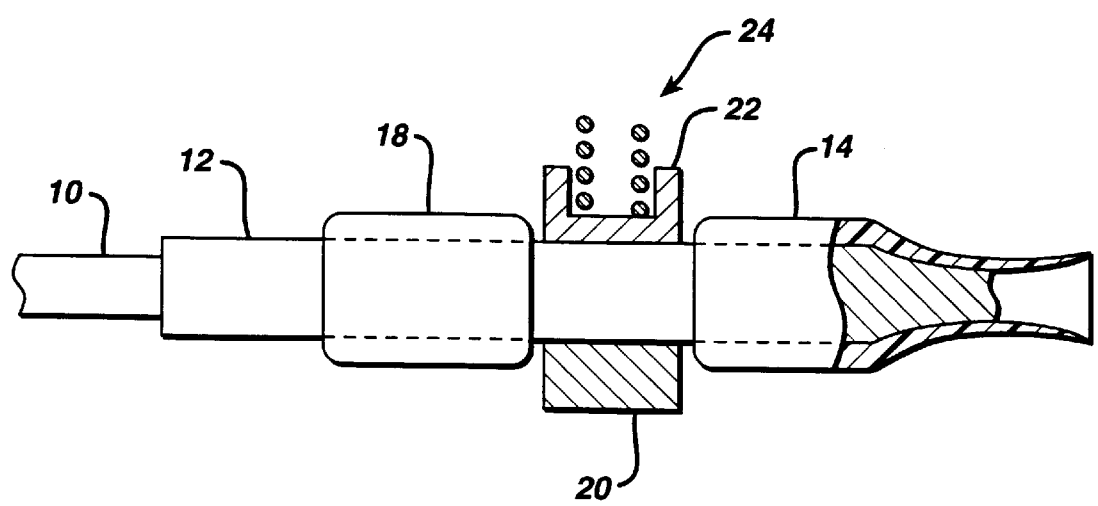
FIG. 2 is a plan view in partial cross section of an alternative embodiment of the present invention attached to a pacemaker contact.

FIG. 2 depicts a schematic of an alternate embodiment of the present invention attached to a pacemaker contact (shown in cross section). For the geometry of typical pacemakers, insulator 14 is about 12 mm long. In addition to insulator 14, the embodiment of FIG. 2 has optional insulator 18. As shown, insulator 18 does not extend to that end of shaft 12 which is attached to wire 10. Since the wire attachment is typically accomplished by swaging, if a polymer coating extended to the end of the shaft, it would be crushed in the swaging process. This would be cosmetically undesirable. An alternative is for insulator 18 to be very thin, applied by anodizing or oxidation, for example. In that case, the insulator would preferably extend to the end of the shaft. As mentioned earlier, two electrodes are used in a setup. Extending insulator 18 to the end of the shaft thus provides additional protection from inadvertent shorting of the two shafts that protrude from a pacemaker. Furthermore, insulation and connector contacts may be color coded to help ensure proper connection of the two electrodes. Conventionally, the ground (or "common") electrode would have black insulation and the positive (or "signal") electrode would have red insulation.

Electrical contact with the pacemaker is effected by contacts 20 and 22, with contact enhanced by spring 24. The contact shown is a simplified depiction of part of a Medtronic pacemaker (5375 Demand Pulse Generator), but pacemakers using other types of contacts, such as a set screw in place of the spring, for example, are also suitable for use with the invention. To the extent that pacemaker connectors differ, the pattern of insulation must, of course, be adapted for the particular pacemaker that is to be used. Multiple patterns can be applied to a single needle shaft, with corresponding multiple weakened zones. Note that insulator 14 provides some (desirable) resistance to pulling the wire out of the contact.

I claim:

1. A surgical electrode comprising
   a) an electrically conductive wire,
   b) means for making electrical contact with a heart, attached to and in electrical contact with one end of the wire,
   c) a surgical needle in electrical contact with the opposite end of the wire, the surgical needle comprising
      i) a blunt first end and sharp second end, joined by a shaft, the first end being attached to the wire,
      ii) a predetermined point on the shaft, defining a first section lying between the point and the blunt end of the needle and a second section lying between the point and the sharp end of the needle, and
      iii) an electrical insulator that extends around the shaft from a first location in the first section at least to the predetermined point.

2. The surgical electrode of claim 1 in which the shaft has, at the predetermined point, a weakened zone at which the needle may readily be broken.

3. The surgical electrode of claim 2 in which the insulator extends a short distance into the second section, whereby substantially no part of the insulator remains with the second section when the needle is broken at the weakened zone.

4. The surgical electrode of claim 3 in which the insulator extends about 0.1 mm to about 1 mm into the second section.

5. The surgical electrode of claim 1 in which the electrical insulator comprises an insulating coating.

6. The surgical electrode of claim 3 in which the insulating coating is of a material selected from the group consisting of poly-xylylene, fluoropolymers, nylon, vinyl, epoxy, urethane, polyamide, polyester, acrylic, silicone, phenylene sulfide, and polyamideimide.

7. The surgical electrode of claim 6 in which the insulating coating comprises poly-xylylene.

8. The surgical electrode of claim 1 in which the insulator extends about 12 mm into the first section.

9. The surgical electrode of claim 1, further comprising a second insulator, entirely in the first section and separated from the first insulator by a section of wire that is not insulated.

10. The surgical electrode of claim 1 in which the insulator is color coded to identify it as either a ground or positive electrode.

* * * * *